United States Patent [19]

Siposs

[11] 4,398,908
[45] Aug. 16, 1983

[54] INSULIN DELIVERY SYSTEM

[76] Inventor: George G. Siposs, 2855 Velasco La., Costa Mesa, Calif. 92626

[21] Appl. No.: 210,780

[22] Filed: Nov. 28, 1980

[51] Int. Cl.³ .................. A61M 5/00; F04B 43/08; F16K 15/16

[52] U.S. Cl. .................................. 604/31; 604/34; 604/250; 417/474; 137/855; 137/512; 128/12

[58] Field of Search .................. 128/260, 214 R, 213, 128/214 F, DIG. 12, 209, 274; 137/512, 844, 848, 856; 417/474, 478

[56] References Cited

U.S. PATENT DOCUMENTS

| | | | |
|---|---|---|---|
| 2,888,877 | 6/1959 | Shellman et al. | 417/474 X |
| 2,896,840 | 7/1959 | Hendry | 137/855 X |
| 3,902,490 | 9/1975 | Jacobsen et al. | 128/214 F |
| 4,184,815 | 1/1980 | Casson et al. | 128/214 F X |
| 4,191,181 | 3/1980 | Franetzki et al. | 128/DIG. 12 X |
| 4,215,689 | 8/1980 | Akiyama et al. | 128/213 R X |
| 4,274,407 | 6/1981 | Scarlett | 128/213 R |

OTHER PUBLICATIONS

K. W. Mitchell, A Small Stroke-Volume Incremental Injection Pump, Controlled by a Physiological Signal, Phys. Med. Biol., 1980, vol. 25, No. 3, 563–565.

Primary Examiner—Stephen C. Pellegrino
Attorney, Agent, or Firm—Allen A. Dicke, Jr.

[57] ABSTRACT

Insulin delivery system comprises insulin reservoir, pump and subcutaneous needle. Pump is electromechanically-driven at a preselectable fixed rate and can be additionally actuated to deliver a preprandial bolus of selected dosage.

16 Claims, 11 Drawing Figures

U.S. Patent  Aug. 16, 1983  Sheet 1 of 2  4,398,908
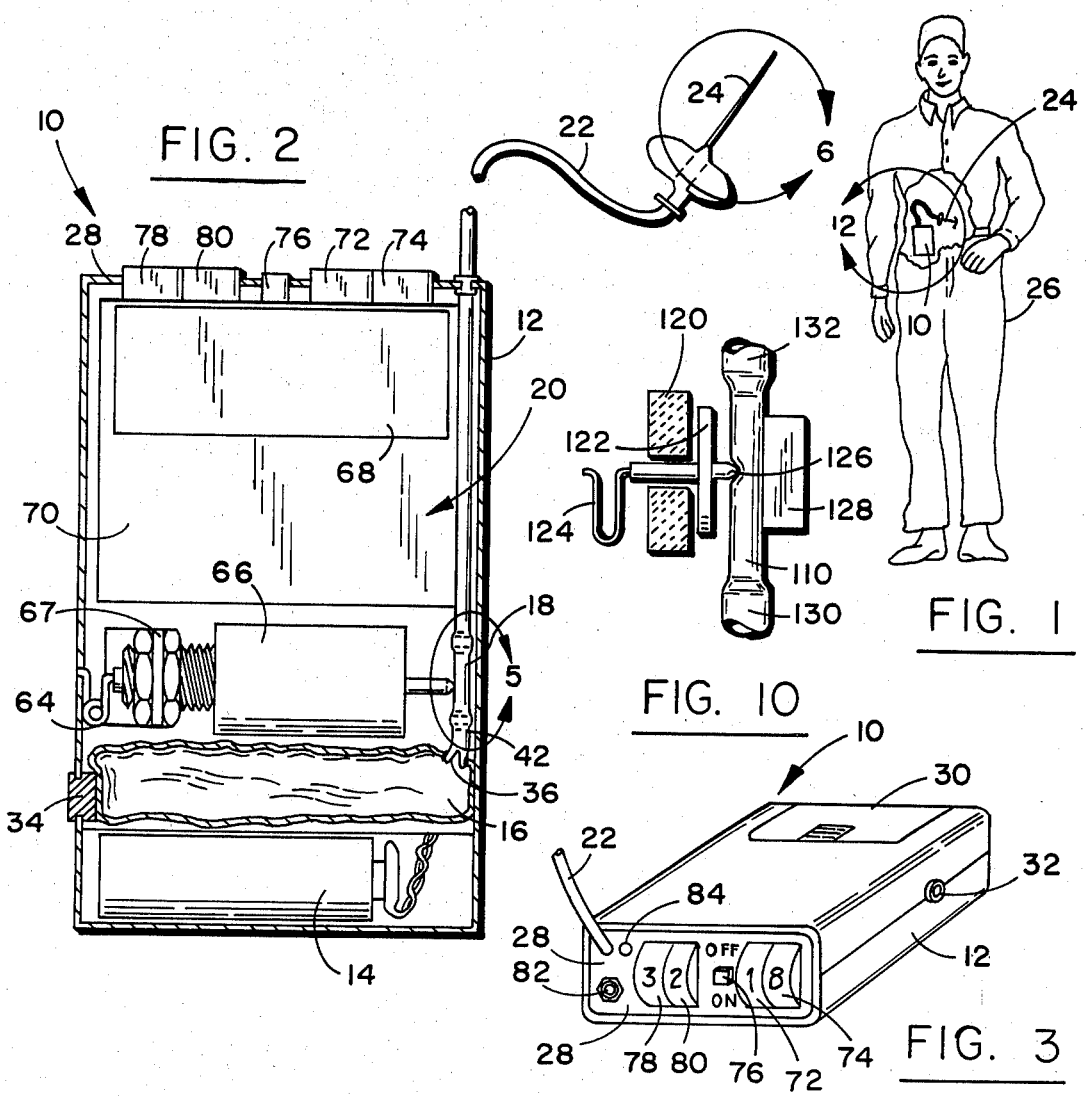
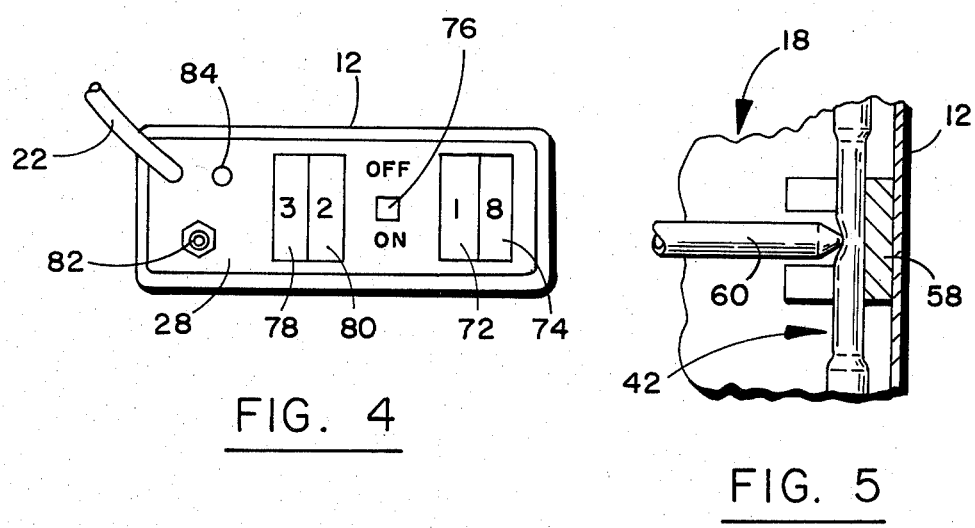

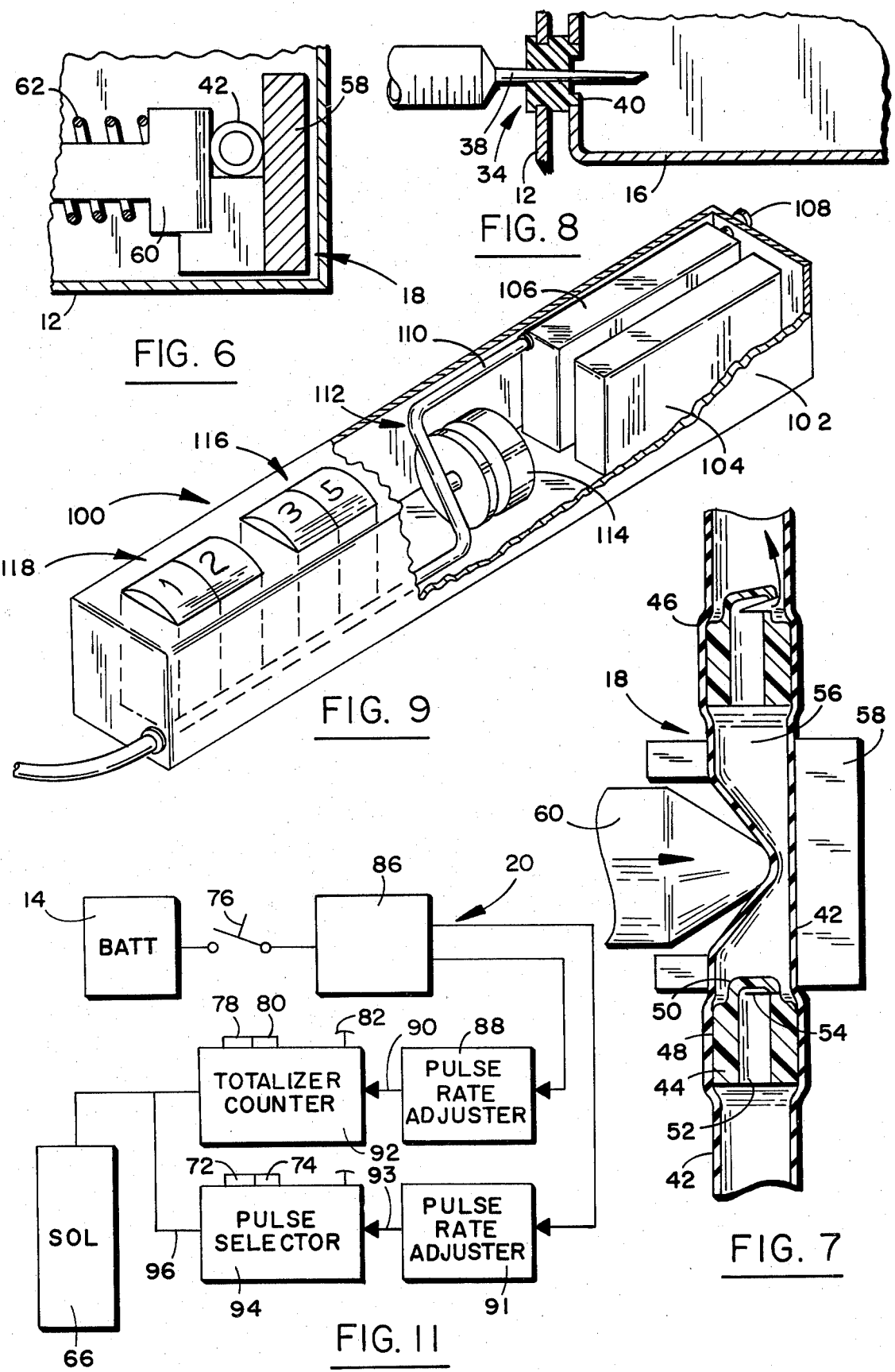

INSULIN DELIVERY SYSTEM

BACKGROUND

This invention is directed to an insulin delivery system which includes a reservoir, a pump and a control system which delivers insulin at a constant rate in accordance with the basal metabolic need, and in preprandial doses so that insulin is delivered to the body in accordance with bodily need.

The preferred embodiment of this invention is in the delivery of insulin, and the invention is described as an insulin delivery system throughout this specification. However, it is clear that it is useful for the delivery of other medications to the body. For example, Heparin can be usefully delivered by this system. Furthermore, chemotherapy medication can be administered and controlled by the delivery system of this invention. Thus, any medication which should be delivered to the patient throughout the day can be properly administered by this delivery system.

The pump, with or without the disclosed reservoir could be used to inject a radio-opaque medium for arteriography, which is a procedure where the physicians inject a dye in unision with the heartbeats so the progress of the dye can be followed on X-ray. The present pump is such that it can deliver a pulse as a reaction to an outside signal. Thus, an EKG signal can trigger the pump to deliver the dye into the vascular system each time the heart beats. The physicians can use this to detect where the coronary arteries are restricted or plugged.

When delivering insulin, as in the preferred embodiment of the delivery system of this invention, should an implanted continuous glucose sensor become successful and reliable, the output of the sensor can be used to trigger the pump in the delivery system of this invention. The pump is designed so that it can proportionately dispense insulin or other medication in accordance with the pump and drive signal, and this signal can be based on a measured or sensed bodily need.

Physicians have found that when a medication is delivered to the body of the patient in very small doses regularly delivered around the clock, the medical effect is better than if the medication is injected in relatively large, discrete boluses. As a result, a number of devices have been designed which are intended to administer medication at a constant rate. One such prior art device is a syringe pump. A screw feed advances the syringe plunger and thus controls the rate of infusion. This structure requires a substantial amount of power to drive the plunger, and thus the drive motor and the battery are bulky and difficult to conveniently carry on the person. The presently leading screw fit syringe plunger type of mechanism is AUTO-SYRINGE. The structure is large and weighty, and the controls are awkward to manage because they require several calculations and corrections to arrive at the flow rate adjustment. Furthermore, the adjustments are made in discrete steps, allowing little resolution or fineness in control. Additionally, the syringe is exposed and thus can be damaged while the patient wears the syringe. Another commercially available device which employs the same syringe principle is the Mill-Hill Pump which has been developed in England.

A third commercially available device represents a different design approach and is made by Siemens in Germany. The Siemens medication dispenser uses a pump which is a roller pump to propel the medication in the tube. This has as a major disadvantage that, whenever the roller leaves the tubing (as it is supported in its circular arcuate track), the tubing expands and thus the delivery of the medication is slowed down, is stopped or may even be drawn backwards. The roller pump always has a cyclic output. Thus, when such a pump is stepped, the output is not necessarily repeatable. For this reason, the roller pump is not suitable for a precise metering application such as insulin injection. Furthermore, such a roller pump requires a substantial amount of power and thus requires a large battery or frequent battery changes. These pumps are "progressive, non-valved" pumps whereas the invention described herein is a "repeating, valved" pump.

These pumps are "progressive, non-valved" pumps whereas the invention described herein is a "repeating, valved" pump.

Thus, there is need for an insulin delivery system which includes a pump that accurately delivers small increments of liquid medication. Such a pump requires a small chamber because of the small volume pumped to each stroke, and requires properly operating valves which are easily actuated and which prevent reverse flow.

SUMMARY

In order to aid in the understanding of this invention, it can be stated in essentially summary form that it is directed to a liquid medication reciprocating delivery system. The system comprises a reservoir, a medication delivery tube, a pump for pumping increments of medication from the reservoir to the tube and a pump controller for controlling the pump in a first, preselected, constant delivery rate mode and a second mode where the pump delivers on demand a preselected quantity of medication.

It is thus an object of this invention to provide a delivery system which is particularly useful for the delivery of insulin and other similar medications wherein a preselected constant rate medication delivery rate is desired, with the delivery rate being supplemented by delivery on demand of additional boluses of medication. It is another object of this invention to provide an insulin delivery system which provides a slow, base-rate delivery of insulin as required by the basal metabolic delivery, and a preselectable, high-rate, on-demand preprandial delivery. It is a further object to provide an insulin delivery system of self-contained construction with a reservoir, pump, power supply and controls to deliver insulin as individually required. It is a system to deliver insulin as individual required. It is a further object to provide a medication delivery system which is capable of delivering various kinds of medication at a preselected delivery rate.

It is another object of this invention to provide a light, simple, portable liquid-medication pumping system which can be connected to a hypodermic needle or a cannula inserted into a vein to dispense medication such as insulin, heparin, chemotherapy medication and the like, to the patient's body at precisely predetermined intervals and at predetermined dosages, around the clock. It is a further object to provide a device which also enables the user to inject a larger and precisely measured dosage of the same medication whenever a switch is actuated. It is a further object of this invention to provide a permanent dispensing system which operates in connection with a disposable low-cost medication reservoir with a delivery tube and with a pump chamber and valves in association with the delivery tube.

Other objects and advantages of this invention will become apparent from a study of the following portion of the specification, the claims and the attached drawings.

BRIEF DESCRIPTION OF THE DRAWINGS

FIG. 1 is a perspective view of the insulin delivery system of this invention, as worn by a user.

FIG. 2 is a plan view of the first preferred embodiment of the delivery system, with the cover removed to show the interior structure, and with parts broken away and parts taken in section.

FIG. 3 is an isometric view, principally of the top of the insulin delivery system of FIG. 2.

FIG. 4 is an end view thereof.

FIG. 5 is an enlarged view of the pumping section.

FIG. 6 is a further enlarged view of the pump, taken as a section transverse to the tubing.

FIG. 7 is a further enlarged view of the pump, taken as a section longitudinally through the tubing.

FIG. 8 is a section through the filling port of the reservoir, with parts broken away.

FIG. 9 is an isometric view of a second preferred embodiment of the insulin delivery system in accordance with this invention.

FIG. 10 is an enlarged view of the medication dispensing pump as used in the delivery system of FIG. 9.

FIG. 11 is an electric schematic diagram of the control system for controlling the pump.

DESCRIPTION OF THE PREFERRED EMBODIMENT

The first preferred embodiment of the insulin and other medication delivery system of this invention is generally indicated at 10 in FIGS. 1 and 2. As is seen in these figures, the delivery system 10 comprises a housing 12 which contains a power supply in the form of battery 14, a medication storage in the form of reservoir 16, pump 18, and pump control system 20. The output of pump 18 goes to delivery tube 22 which carries subcutaneous needle 24 on its end. As is seen in FIG. 1, the housing of the delivery system 10 is worn on the belt of patient 26, and the needle 24 is subcutaneously inserted in the patient at a position above reservoir 16. It may be taped in place by means of the wings on the needle near the umbilicus.

Considering the system one structural element at a time, housing 12 is a rigid, hollow structure which contains the major part of the system. It is preferably a pocket-sized device, preferably not much larger in size than a package of cigarettes. It is intended to be worn vertically, as illustrated in FIG. 1 and its top 28, see FIGS. 3 and 4, carries thereon those external controls which can be adjusted by the patient. Housing 12 also has access hatch 30 for access to the batteries 14 and may have an external battery recharging jack 32 by which the batteries 14 can be recharged from an external source of electric power, or battery can be removed for recharging.

Reservoir 16 is in the form of a flexible bladder made of flexible limp polymer composition material. It has an inlet 34 and an outlet 36. The limp flexibility of the soft pouch of the bladder permits collapse of the reservoir as liquid medication is withdrawn therefrom. Inlet 34 is a soft plug 40 through which a refilling needle 38 can be inserted. The plug may be attached in the sidewall of housing 12 so that it is firmly supported. The bladder of reservoir 16 is connected to the plug.

In order to make the device leak-proof and non-gravity dependent, the reservoir has no air vent. The reservoir is soft and compliant so that as liquid is withdrawn from it, the reservoir collapses. The reservoir bag is not rubber, because if it were rubber, it would have its own spring force that would provide its own pumping action and that could make a difference in the delivery rate between full and empty states of the reservoir. Accordingly, the limp material of the reservoir is neutral in force.

Outlet 36 from reservoir 16 is a flexible tube attached to the reservoir, by heatsealing or by adhesive means. The flexible tube which serves as the reservoir outlet is indicated at 42 in FIGS. 2, 5 and 7. Flexible tube 42 is part of the same continuous flexible tube that extends continuously from the reservoir outlet 36 through pump 18 and extends as delivery tube 22 to needle 24. It is preferably a onepiece structure, but, of course, can be joined if helpful for manufacturing purposes.

Pump 18 is shown in more detail in FIGS. 5, 6 and 7. Inlet and outlet valves 44 and 46 are shown in detail in FIG. 7. Inlet valve 44 is closer to the reservoir and comprises a body 48 of flexible material in cupshaped form. The body is substantially cylindrical on the outside and at its outlet end has a reduced diameter boss 50. Bore 52 extends from the bottom of the body upwards into the inside of boss 50. The cylindrical bore 52 provides a thicker wall through the lower part of the body and a substantially uniform thickness wall around the boss and through the closure at the top of the boss and the bore. The valve body is molded of a resilient material with the boss closed. Slit 54 is made after the molding is complete. Slit 54 is made with a thin, sharp blade such as a razor to form a slit perpendicular to the axis of the body, which is on the center line of the tube 42. Valve opening slit 54 extends about two-thirds the way across boss 50. It is a neutral valve which is neither resiliently biased shut or resiliently biased open. Therefore, it opens with the smallest pressure drop in the forward direction and closes with the smallest pressure drop in the reverse direction. The boss end of the valve is the outlet end, and the two valves 46 and 48 are positioned with their bosses in the upwardly directed position. When volume in tube 42 between valves 46 and 48 is decreased, then fluid is discharged upwardly through valve 46. When this volume is subsequently increased, liquid is drawn upwards from reservoir 16 through valve 48 into the volume 56 because natural resilience of tube 42 causes it to resume its shape.

Tube support 58 is L-shaped, with tube 42 resting on the elbow of the L. The lower foot of the L is notched to permit wedge-shaped pumping blade 60 to move forward to both compress the tube 42 between valves 46 and 48 and to pinch off the tube against the back of support 58 at the end of the pumping stroke. The "pinched closed" position is the non-actuated position. Tube closure is assured by its spring 64 in the embodiment of FIG. 2, or spring 62 in the embodiment of FIG. 6. Solenoid 66 is mounted on bracket 67 by a nut on each side of the bracket. The plunger of solenoid 66 carries pumping blade 60 and when energized, solenoid 66 withdraws the pumping blade 60 from the tube to permit the tube to draw liquid from the reservoir through the lower valve 48.

The basic pumping action is achieved by the heart ventriclelike pumping chamber 56 which is compressed by the spring-driven wedge 60 and is enlarged by solenoid actuation. The inlet and outlet valves of the chamber 56 act much like the left ventricle of the heart. The soft tubing which forms the chamber has sufficient resiliency and memory to return to the cylindrical tubular condition so that, when the pumping blade 60 is pulled back, the chamber can draw in the liquid from the reservoir. Thus, a predetermined amount of liquid can be pumped with each stroke. Each pump delivery is basically the same as any other, and with the cutoff provided at the end of the stroke, the pumping action is precisely repetitive, positive, non-draining and reliable. It is, thus, a repeating valved pump. If desired, the solenoid stroke can be micrometrically adjusted by means of an adjustable stop between the tube support 58 and the solenoid plunger, or by the solenoid support nuts, see FIG. 2.

The pump control system 20 periodically energizes solenoid 66 to control the pump delivery. FIG. 2 shows a switch bank 68 which is associated with a printed circuitboard 70 which carries thereon the electronics which control the pumping action. Switch bank 68 has a pair of switch dials 72 and 74 which are rotary switches having 10 positions so that any value from 00 to 99 can be selected. These switch dials are used to select the base delivery rate. Switch bank 68 also has an on-off switch 76 which controls battery power to the whole pump control system. Switch bank 68 also carries rotary switches 78 and 80 which are digital switches for setting the preprandial dosage and are settable from 00 to 99. In addition, the top 28 carries preprandial actuator switch 82 and pump pulse indicator light 84.

Referring to FIG. 11, the pump control system includes a timing oscillator 86 which is energized from battery 14 through on-off switch 76. The oscillator 86 can be an L-C or R-C oscillator, or some other type of compact, low-power timing device. The oscillator 86 has two separate output channels respectively dedicated to control preprandial and basal dosage. For the preprandial dosage, oscillator output is divided by pulse rate adjuster 88 so that there are timed pulses in divider output line 90. The pulse rate is selected to the pulse pump rate desired for preprandial dosage. In the present example, a divider output pulse rate of 20 pulses per minute, or pulses with a 3-second interval is selected. This rate is factory preset.

As previously discussed, the pump 18 can be calibrated to deliver a preselected volume per stroke. In the present example, it delivers 0.001 milliliters of liquid per stroke. The most popular insulin is of 100 units strength per milliliter, and thus each pump stroke delivers 0.1 unit of insulin. This is given by way of example, and, of course, the pump strokes and pump chamber size can be configured to suit other medications or other medication concentrations or delivery site requirements.

Totalizer counter 92 carries rotary switches 78 and 80 thereon. These rotary switches are set to a predetermined bolus of insulin as a preprandial dosage. As discussed above, researchers have found the basic bodily need for insulin. They have found that a diabetic needs approximately 0.013 units of insulin per hour per kilogram of body weight. In addition, a preprandial dosage is required for each meal to accommodate for the food taken. Different amounts are taken for each meal, and it has been found that approximately 35 percent of the preprandial dosage should be used for the breakfast dosage, 25 percent for each of the lunch and dinner dosages, and 15 percent for the bedtime snack. Continuing the particular example, a patient who weighs 78 kilograms and presently injects 80 units of insulin daily requires 78×0.013 equals approximately 1 unit of insulin per hour as a basal metabolic rate, which equals 24 units per day. The remainder of the insulin dosage (80 minus 24 equals 56 units) is divided into the 35-25-25-15 percent ratio. Thus, the breakfast dosage will be approximately 20 units;, the lunch and dinner dosages, 14 units each; and 8 units for the snack dosage.

With the pump delivering 0.1 unit per stroke, 200 pump strokes will be required to deliver the preprandial breakfast dosage. Thus, before breakfast the rotary switches 78 and 80 are set for 20 units and the preprandial switch 82 is actuated. Totalizer counter 92 then passes the 20 pulses per minute in line 90 to successively energize solenoid 66 until the 200 pulses are counted to provide the 20 units of insulin. Thereupon, the circuit reverts to the basal rate.

When lunchtime comes, the patient resets the rotary switches 78 and 80 to the 14 units required for the lunch preprandial dosage and then initiates that dosage by pressing button 82. The switch setting is appropriately repeated for each preprandial dosage. The rotary switches 78 and 80 are preferably calibrated in insulin units, rather than the number of pulses, and the totalizer counter 92 provides the appropriate correlation so that, when 20 insulin units are to be delivered and 20 is numerically set on the rotary switches 78 and 80, then 200 pulses, representing 0.1 unit of insulin per pulse are counted, for a total of 20 units delivered.

As discussed above, it has been found that a diabetic needs approximately 0.013 unit of insulin per hour per kilogram of body weight. In the example, a patient who weighs 78 kilograms requires 78×0.013 equals 1 unit of insulin per hour. Pulse rate adjuster 91 supplies pulses with a 36 second period by line 93 to pulse selector 94. Pulse selector 94 controls delivery of the basal dosage. Rotary switches 72 and 74 on pulse selector 94 are used to set the desired rate of delivery. In the example, 1 unit per hour is required as the basal metabolic rate, and this figure is looked up in a conversion table to provide the switch settings on rotary selector switches 72 and 74. Pulse selector 94 selects the intervals between successive pulses. Each output pulse actuates solenoid 66 through line 96. In the present case, when each pump stroke delivers 0.1 unit of insulin and 1 unit per hour are required as basal medication, then the frequency in line 96 at the output of pulse selector 94 is 10 pulses per hour. In this way, the metabolic dosage continues to provide a more uniform insulin dosage throughout the day. The slow base rate delivery of insulin interspersed with a preset high rate ondemand preprandial delivery has been tested and found to result in better control in several patients.

If it is not preferred that the reservoir 16 be refilled through inlet 34, the entire system is designed for complete exchange of the parts which are in contact with the medication. For example, when the cover is removed from housing 12, reservoir 16, tube 22 including pump 18 and needle 24 can be removed as a unit. A full and sterile reservoir and pumping system can be put in place, simply laying the pumping tube on its support 58 for complete replacement of the portions which need to be sterile, or the hypodermic needle alone can be detached and replaced so that the disposable part of the system has a low cost to the patient.

The on-off switch 76 is provided so that should a mistake be made in choosing the proper prepandial dosage, the pump can be turned off to stop dosage until the proper amount is dialed into the preselector switch. Pulse indicator 84 is a small light that lights every time the solenoid is energized to indicate to the patient that the pump is working. A warning buzzer is provided in the circuit in such a manner that it buzzes when the battery voltage reaches a preselected low value. Thus, as the battery reaches a state of near discharge, the warning buzzer comes on. However, there is a sufficient battery charge remaining that a few hundred pulses can still be made before the battery becomes completely ineffective. The battery can be changed by inserting a previously recharged or a fresh battery. Separate recharging of rechargeable batteries is preferred to maintain patient mobility.

FIG. 9 illustrates a second preferred embodiment of the insulin delivery system of this invention which is generally indicated at 100. Insulin delivery system 100 is functionally the same as insulin delivery system 10, but is configured to occupy a long, narrow housing of square, rectangular or circular cross section 102. Delivery system 100 has battery 104. It has reservoir 106 with its fill port 108, and delivery tube 110. The delivery tube passes pump 112 with its solenoid 114 and exits past switch sets 116 and 118 out of the near end of the housing in FIG. 9. The switch sets 116 and 118 are employed to set the prepandial boluses and basal metabolic rate, respectively. Furthermore, insulin delivery system 100 has the switches and indicators of the system 10. In order to fit the insulin delivery system into a long, narrow housing as shown, the pumping solenoid is a flat, rather than a long structure. In FIG. 10, the solenoid coil 120 is illustrated as a flat, annular coil which draws its disk-like armature 122 to the left, when energized. Spring 124 urges armature 122 to the right, so that its wedge-shaped pumping blade 126 acts on tube 110. Tube support 128 supports the tube in the manner previously indicated. Inlet and outlet valves 130 and 132 are the same as the valves in FIG. 7, so that the pump works the same way as illustrated in FIG. 7. Thus, insulin delivery system 100 has the same components and has the same controls and functions as the insulin delivery system 10. In some cases, the configuration generally illustrated in FIG. 9 is more conveniently carried, e.g., like a fountain pen.

This invention has been described in its presently contemplated best mode, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A medication delivery system comprising:
   a portable housing;
   a medication reservoir in association with said housing;
   a repeating, valved medication pump in association with said housing and connected to said reservoir, said pump comprising:
   a tube;
   inlet and outlet valves in said tube, said valves allowing flow only from said reservoir to said delivery tube;
   a tube support, said tube being engaged against said support between said valves;
   a movable pumping blade engaging said tube opposite said support for alternately pressing and releasing said tube against said support; and
   means for moving said blade, said blade having a rest position so that when said pump is inactive, said tube is closed to prevent said reservoir from draining;
   a delivery tube extending from said pump so that operation of said pump draws medication from said reservoir and delivers it out of said delivery tube, said delivery tube extending from said housing for the delivery of medication to a patient; and
   digital control means for said pump comprising means for producing pulses at a substantially constant pulse rate, a pulse counter connected to receive pulses from said means for producing pulses, said blade-moving means being connected to said pulse counter so that said moving means pulses for each pulse passed by said pulse counter, said pulse counter counting and passing a predetermined number of pulses from said means for producing pulses and thereafter passing no further pulses to said moving means until said pulse counter is reset.

2. The medication system of claim 1 wherein said pump volume is controlled by the stroke length of said blade between inlet and outlet valves.

3. The medication delivery system of claim 2 wherein at least one of said valves has a tubular body having a boss end and having an internal bore extending substantially to said boss end and a valve slit extending transversely through a portion of said boss end from the external portion thereof to said bore to provide a movable flap.

4. The medication delivery system of claim 3 wherein said body is cylindrical and said boss end is of smaller diameter than said body, said slit being transversely directed through said boss end.

5. The medication delivery system of claim 1 wherein said pumping blade has a controlled stroke so that the change in volume of said pumping volume per stroke of said pumping blade can be varied.

6. The medication delivery system of claim 1, said moving means comprising:
   a solenoid connected to withdraw said pumping blade away from support;
   a spring connected to resiliently urge said blade towards said tube support;
   and said pump control system is connected to control said solenoid.

7. The delivery system of claim 1 wherein said reservoir is a limp, neutral-pressure reservoir.

8. The medical delivery system of claim 7 wherein said reservoir has a soft resilient inlet plug therein through which a hypodermic needle can be inserted to refill said reservoir.

9. The medication delivery system of claim 7 wherein at least one of said reservoir, said pump, said delivery tube and an injection needle on said delivery tube are removable and replaceable as an individual, sterile unit.

10. The medication delivery system of claim 7 wherein said reservoir, said valves, said pump and said delivery tube are removable and replaceable as a unit so that a filled and sterile unit can be substituted for an exhausted unit.

11. The medication delivery system of claim 1 wherein a removable, replaceable sterile needle is connected to the delivery end of said delivery tube for insertion into a patient for the delivery of medication to the patient.

12. A medication delivery system comprising:
   a portable housing;
   a medication reservoir in association with said housing;
   a repeating, valved medication pump in association with said housing and connected to said reservoir, said pump comprising:
   a tube;
   inlet and outlet valves in said tube, said valves allowing flow only from said reservoir to said delivery tube;
   a tube support, said tube being engaged against said support between said valves;
   a movable pumping blade engaging said tube opposite said support for alternately pressing and releasing said tube against said support; and
   means for moving said blade, said blade having a rest position so that when said pump is inactive, said tube is closed to prevent said reservoir from draining;
   a pulse counter connected to receive pulses from said means for producing pulses, said pulse counter being presettable to pass a predetermined number of pulses which are proportional to the number of units of medication, said blade-moving means being connected to said pulse counter so that said moving means pulses for each pulse passed by said pulse counter, said pulse counter counting and passing a predetermined number of pulses from said means for producing pulses and thereafter passing no further pulses to said moving means until said pulse counter is reset.

13. The medication delivery system of claim 12 wherein said pulse counter has selector devices thereon for adjusting to preset the number of pulses passed by said counter.

14. A medication delivery system comprising:
   a portable housing;
   a medication reservoir in association with said housing;
   a repeating, valved medication pump in association with said housing and connected to said reservoir, said pump comprising:
   a tube;
   inlet and outlet valves in said tube, said valves allowing flow only from said reservoir to said delivery tube;
   a tube support, said tube being engaged against said support between said valves;
   a movable pumping blade engaging said tube opposite said support for alternately pressing and releasing said tube against said support; and
   means for moving said blade, said blade having a rest position so that when said pump is inactive, said tube is closed to prevent said reservoir from draining;
   a delivery tube extending from said pump so that operation of said pump draws medication from said reservoir and delivers it out of said delivery tube, said delivery tube extending from said housing for the delivery of medication to a patient; and
   digital control means for said pump said control means comprising:
   pulse producing means;
   a selectable pulse divider having an input from said means for producing pulses and an output to said blademoving means, said selectable divider dividing the pulse rate at said input to the output pulse rate by a selected ratio so that said pump can be controlled to provide predetermined discrete deliveries of medication.

15. The medication delivery system of claim 14 wherein said selected ratio is adjustable.

16. The medication delivery system of claim 15 wherein said selectable divider has external switches thereon for preselecting the dividing ratio.

* * * * *